(12) United States Patent
Delgado et al.

(10) Patent No.: US 10,096,478 B2
(45) Date of Patent: Oct. 9, 2018

(54) SYSTEM AND METHOD FOR REJUVENATING AN IMAGING SENSOR DEGRADED BY EXPOSURE TO EXTREME ULTRAVIOLET OR DEEP ULTRAVIOLET LIGHT

(71) Applicant: KLA-Tencor Corporation, Milpitas, CA (US)

(72) Inventors: Gildardo Delgado, Livermore, CA (US); Gary Janik, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/860,230

(22) Filed: Apr. 10, 2013

(65) Prior Publication Data

US 2013/0295695 A1 Nov. 7, 2013

Related U.S. Application Data

(60) Provisional application No. 61/623,557, filed on Apr. 12, 2012.

(51) Int. Cl.
*H01L 21/00* (2006.01)
*H01L 21/26* (2006.01)
(Continued)

(52) U.S. Cl.
CPC .......... *H01L 21/26* (2013.01); *G01J 1/0228* (2013.01); *G01J 1/429* (2013.01);
(Continued)

(58) Field of Classification Search
CPC ......... H01L 21/26; G01J 1/0228; G01J 1/429; G01J 2001/0285; G01J 2001/0276; G01N 2021/95676
See application file for complete search history.

(56) References Cited

U.S. PATENT DOCUMENTS

| 7,110,113 B1* | 9/2006 | Janik et al. ................... 356/369 |
| 2002/0154297 A1* | 10/2002 | Noguchi et al. ........... 356/237.3 |

(Continued)

FOREIGN PATENT DOCUMENTS

JP 2004014710 A 1/2004

OTHER PUBLICATIONS

A.E. Delahoy et al., Light-Induced Recovery in a-Si:H Solar Cells, American Institute of Physics Conference Proceedings, vol. 157, Dec. 31, 1987, pp. 263-270.
(Continued)

*Primary Examiner* — Charles Garber
*Assistant Examiner* — Abdulfattah Mustapha
(74) *Attorney, Agent, or Firm* — Suiter Swantz pc llo

(57) ABSTRACT

The present invention for imaging sensor rejuvenation may include a rejuvenation illumination system configured to selectably illuminate a portion of an imaging sensor of an imaging system with illumination suitable for at least partially rejuvenating the imaging sensor degraded by exposure to at least one of extreme ultraviolet light or deep ultraviolet light; and a controller communicatively coupled to the rejuvenation illumination system and configured to direct the rejuvenation illumination system to illuminate the imaging sensor for one or more illumination cycles during a non-imaging state of the imaging sensor.

18 Claims, 4 Drawing Sheets

(51) Int. Cl.
*G01J 1/42* (2006.01)
*G01N 21/956* (2006.01)
*G01J 1/02* (2006.01)

(52) U.S. Cl.
CPC ................. *G01J 2001/0276* (2013.01); *G01J 2001/0285* (2013.01); *G01N 2021/95676* (2013.01)

(56) References Cited

U.S. PATENT DOCUMENTS

| | | | |
|---|---|---|---|
| 2004/0211894 A1 | 10/2004 | Hother et al. | |
| 2005/0110987 A1* | 5/2005 | Furman | G01N 21/8806 356/237.4 |
| 2007/0030466 A1* | 2/2007 | Shuichi | 355/30 |
| 2007/0158636 A1* | 7/2007 | Tezuka | 257/10 |
| 2007/0263999 A1 | 11/2007 | Keam | |
| 2008/0058602 A1 | 3/2008 | Landry | |
| 2008/0158348 A1 | 7/2008 | Karpen et al. | |
| 2008/0203326 A1 | 8/2008 | Neukirch | |
| 2011/0075928 A1* | 3/2011 | Jeong | G02B 27/58 382/181 |
| 2011/0102565 A1* | 5/2011 | Wang | G01J 3/02 348/61 |
| 2012/0235049 A1* | 9/2012 | Wang | G01N 21/956 250/372 |

OTHER PUBLICATIONS

Supplementary European Search Report dated Dec. 8, 2015 for EP 13 77 5277, 8 pages.

* cited by examiner

SYSTEM AND METHOD FOR REJUVENATING AN IMAGING SENSOR DEGRADED BY EXPOSURE TO EXTREME ULTRAVIOLET OR DEEP ULTRAVIOLET LIGHT

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional patent application entitled METHODS FOR REJUVENATING DEGRADED CCD SENSOR, naming Gary Janik and Gil Delgado, as inventors, filed Apr. 12, 2012, Application Ser. No. 61/623,557.

TECHNICAL FIELD

The present invention generally relates to a method and system for rejuvenating or repairing an imaging sensor degraded by high energy light exposure, and, in particular, a method and system for rejuvenating or repairing an imaging sensor of a mask or wafer inspection tool degraded by extreme ultraviolet light or deep ultraviolet light exposure.

BACKGROUND

Inspection tools and procedures are commonly implemented during the fabrication of semiconductor devices. Inspection tools are used at various stages of the semiconductor device fabrication process in order to image semiconductor wafers and the lithography masks used to form the patterns on the semiconductor wafers. Fabricating semiconductor devices such as logic and memory devices typically includes processing a substrate such as a semiconductor wafer using a large number of semiconductor fabrication processes to form various features and multiple levels of the semiconductor devices. In some cases, extreme ultraviolet (EUV) and/or deep ultraviolet (DUV) light are used to image the various features of a given mask or wafer. The exposure of an imaging sensor (e.g., CCD imaging sensor) of an inspection tool to EUV or DUV light may lead to degradation of the given imaging sensor. The degradation of one or more imaging sensors of an inspection tool, in turn, leads to reduced processing and analysis throughput.

There are a number of commonly implemented procedures used to mitigate imaging sensor degradation caused by EUV or DUV light. In one case, previous methods included the operation operating an imaging sensor, such as a CCD, at cryogenic temperatures (e.g., below 100 K). However, the cooling of a given imaging sensor serves problematic for large area, high-speed imaging sensors, which are commonly used in commercial applications. The operation of large area, high-speed sensors commonly generates heat at rates greater than 10 W. In turn, this heat generation exerts a significant thermal load on the cryogenic cooling system. This short fall is compounded by the fact that cryogenic cooling systems are typically expensive, large and cumbersome.

In another case, imaging sensor degradation is commonly countered by simply replacing a given imaging sensor once the imaging sensor has reached a selected level degradation or at pre-selected usage levels based on anticipated degradation. This technique, however, leads to increased downtime of the given inspection tool, reducing efficiency and throughput.

As a result, improved systems and methods for mitigating the impact of image sensor degradation caused by exposure to EUV or DUV light are desirable.

SUMMARY

An apparatus for rejuvenating an imaging sensor degraded by exposure to EUV or DUV light is disclosed. In one aspect, an apparatus may include, but is not limited to, a rejuvenation illumination system configured to selectably illuminate a portion of an imaging sensor of an imaging system with illumination suitable for at least partially rejuvenating the imaging sensor degraded by exposure to at least one of extreme ultraviolet light or deep ultraviolet light; and a controller communicatively coupled to the rejuvenation illumination system and configured to direct the rejuvenation illumination system to illuminate the imaging sensor for one or more illumination cycles during a non-imaging state of the imaging sensor.

A method for rejuvenating an imaging sensor degraded by exposure to EUV or DUV light is disclosed. In one aspect, a method may include, but is not limited to, illuminating a portion of an imaging sensor of an imaging system during a non-imaging state of the imaging sensor with illumination suitable for at least partially rejuvenating the imaging sensor degraded by exposure to at least one of extreme ultraviolet light or deep ultraviolet light; monitoring the temperature of the imaging sensor; and responsive to the monitored temperature of the imaging sensor, establishing or maintaining the temperature of the imaging sensor by adjusting a power output level of illumination impinging on the imaging sensor.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Figure 1A:
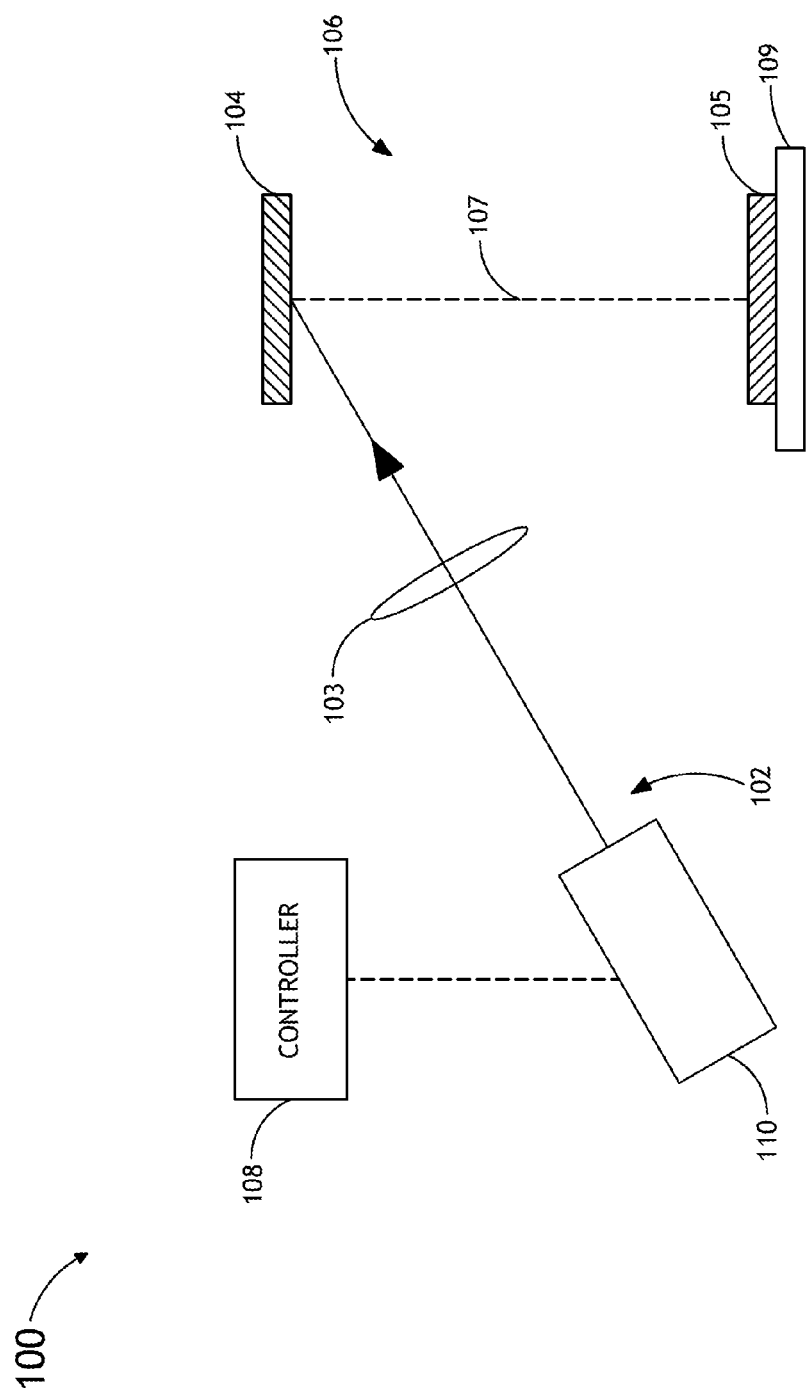
FIG. 1A illustrates a block diagram view of a system for rejuvenating a degraded imaging sensor, in accordance with one embodiment of the present invention.
Figure 1B:
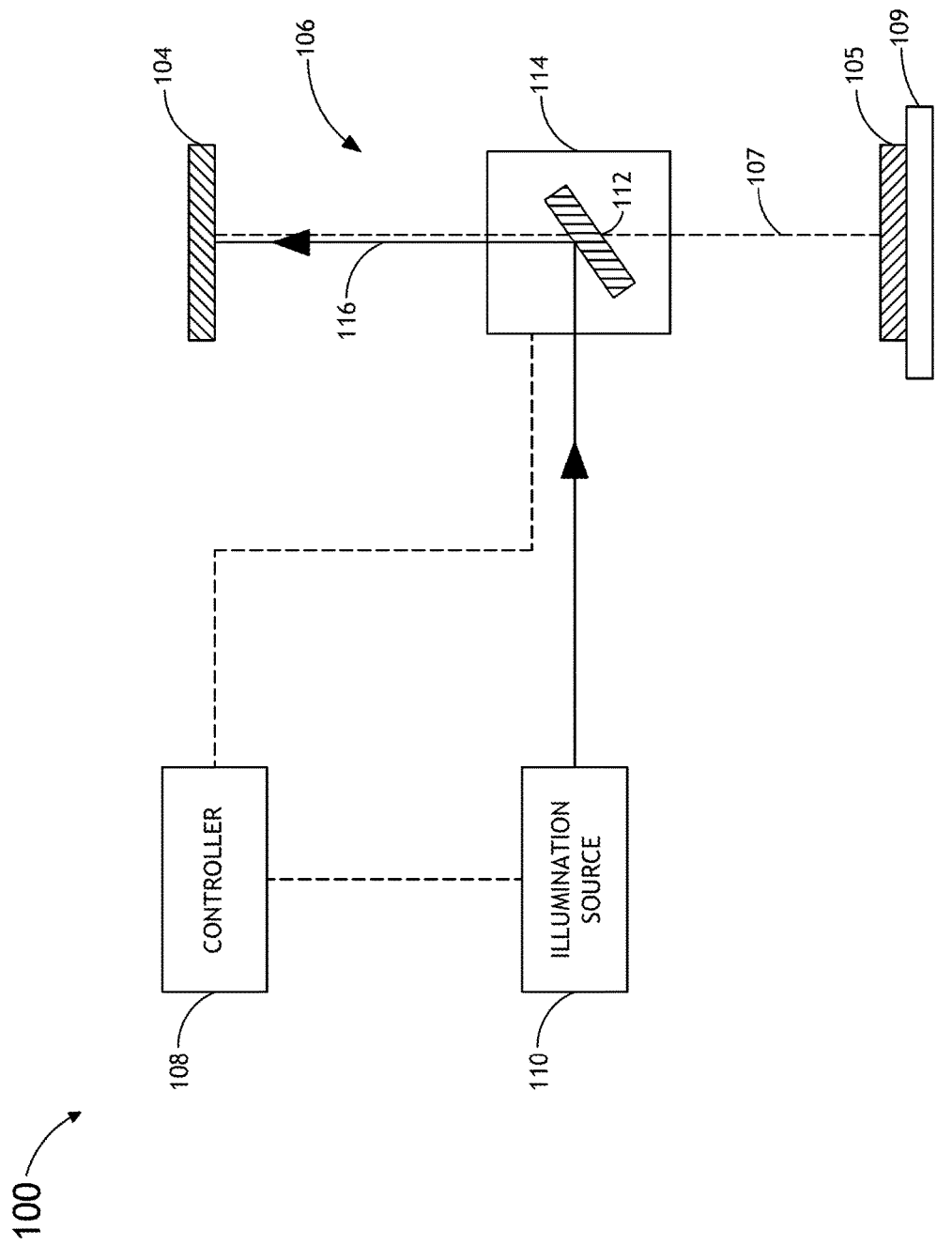
FIG. 1B illustrates a block diagram view of a system for rejuvenating a degraded imaging sensor, in accordance with one embodiment of the present invention.
Figure 1C:
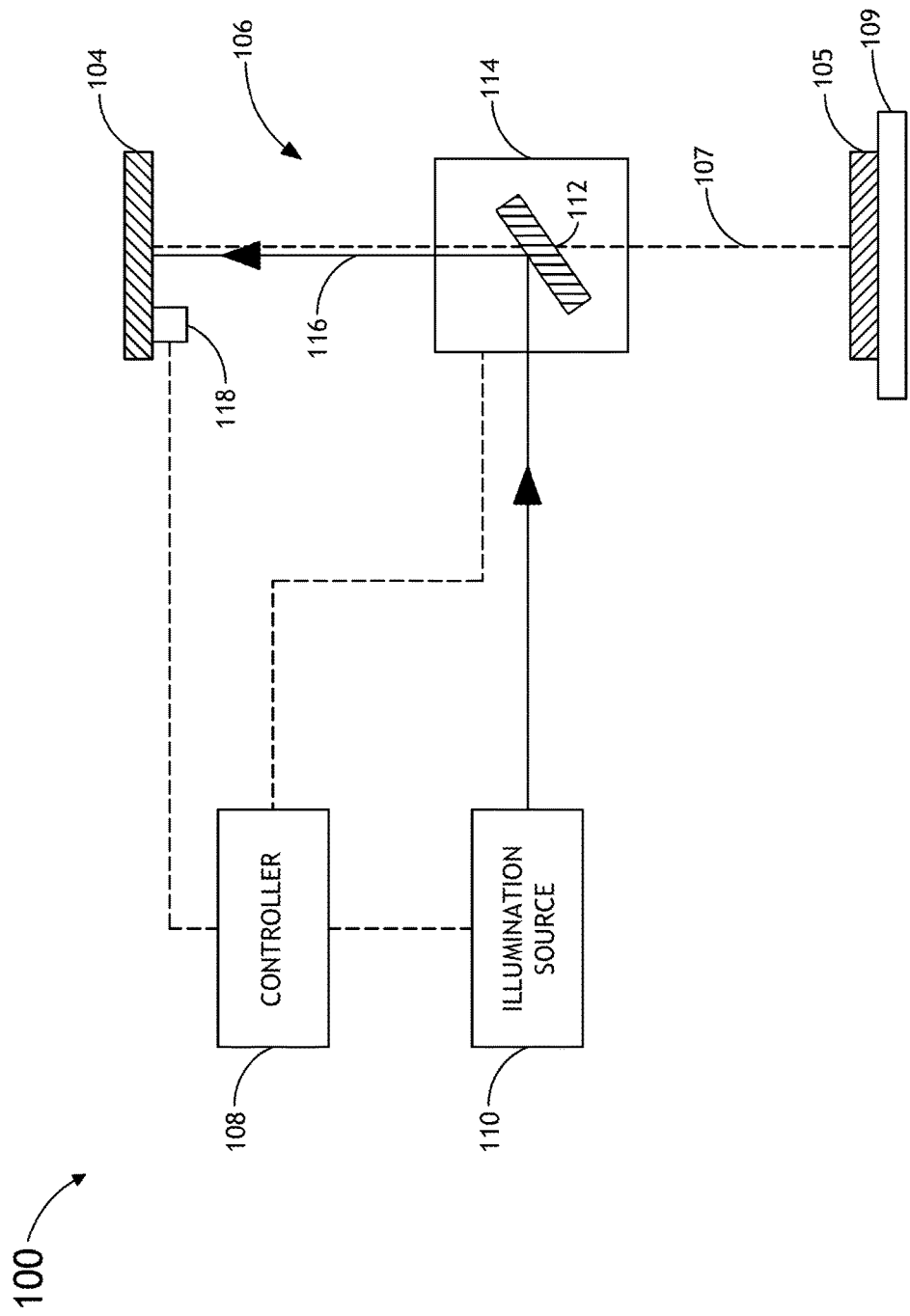
FIG. 1C illustrates a block diagram view of a system for rejuvenating a degraded imaging sensor, in accordance with one embodiment of the present invention.
Figure 2:
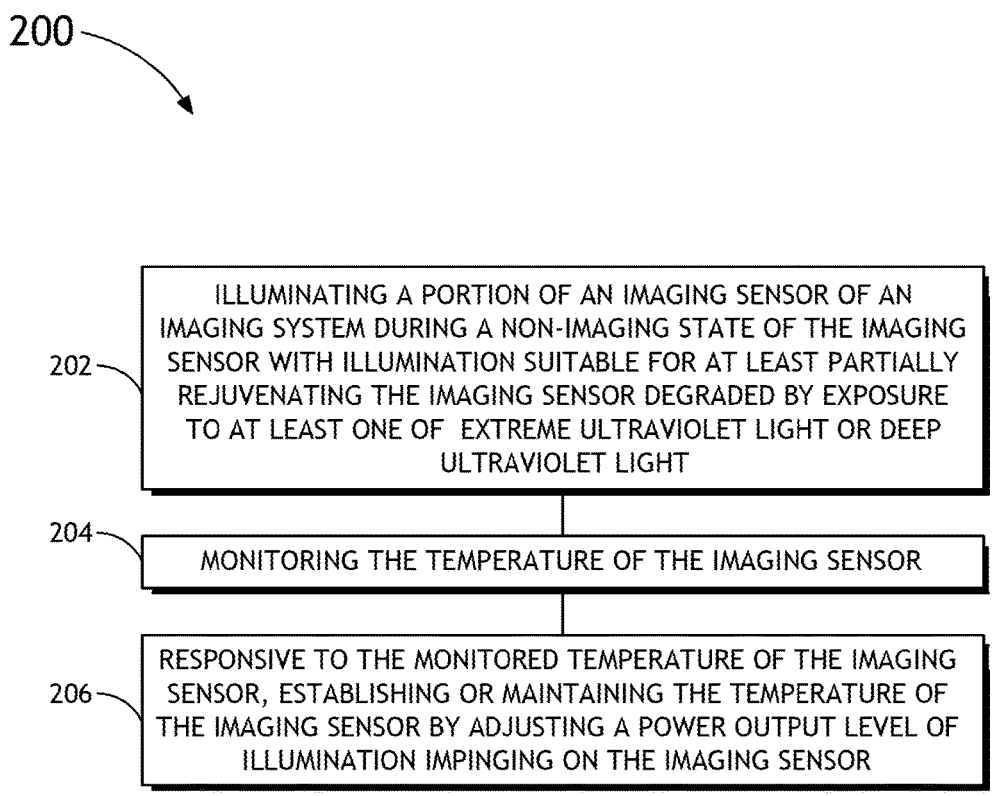
FIG. 2 illustrates a process flow diagram of a method for rejuvenating a degraded imaging sensor, in accordance with one embodiment of the present invention.

Referring generally to FIGS. 1A through 2, a system and method for rejuvenating an imaging sensor degraded by exposure to extreme ultraviolet (EUV) or deep ultraviolet (DUV) light is described in accordance with the present invention. The present disclosure is directed toward embodiments for illuminating an imaging sensor (e.g., CCD sensor) of a semiconductor wafer and mask measurement system (e.g., inspection system) degraded by exposure to EUV or DUV light. In this regard, the system of the present invention may selectably illuminate a degraded imaging sensor during non-operation phases of the given imaging or measurement system. It is noted herein that various embodiments of the present invention may be used to rejuvenate (i.e., reverse degradation caused by high energy light exposure) without removing the imaging sensor from the measurement or imaging system. In this regard, the rejuvenation of the imaging sensor may be performed in-situ or ex-situ. The system and method of the present invention includes selectably illuminating the imaging sensor of given measurement or imaging system with near infrared, visible or near ultraviolet light with enough intensity to heat the substrate of the imaging sensor, causing the temperature of the substrate of the imaging sensor to rise and therefore accelerate the imaging sensor rejuvenation process.

FIG. 1A illustrates a block diagram view of the rejuvenating system 100, in accordance with one embodiment of the present invention. In one aspect, the system 100 may include a rejuvenation illumination system 102 configured to selectably illuminate one or more imaging sensors 104 of an imaging system 106. In this regard, the illumination system 102 is suitable for at least partially rejuvenating an imaging sensor degraded by exposure to EUV or DUV light. In another aspect, the system may include a controller 108. In one embodiment, the controller 108 is communicatively coupled (e.g., wireline or wireless coupling) to the rejuvenation illumination system 102. In a further embodiment, the controller 108 is configured to direct, or control, the rejuvenation illumination system 102 in order to illuminate the one or more imaging sensors 104 of the imaging system 106 with one or more cycles of illumination. In another aspect, the controller 108 is configured to cause the rejuvenation illumination system 102 to illuminate the imaging sensor 104 with one or more cycles of illumination (i.e., light) suitable for at least partially rejuvenating the sensor 104. In another aspect, the controller 108 is configured to cause the rejuvenation illumination system 102 to illuminate the one or more imaging sensors 104 during one or more non-imaging states (i.e., imaging sensor is not in operation) of the imaging sensor 104. In this regard, the controller 108 is configured to cause the rejuvenation illumination system 102 to illuminate a given imaging sensor 104 at times when the imaging sensor 104 is not being used by the imaging system 106 for image detection.

In one embodiment of the present invention, the imaging sensor 104 may include a semiconductor based imaging sensor. In one embodiment, the imaging sensor 104 include charged coupled device (CCD) imaging sensor. In a further embodiment, the imaging sensor 104 may include a silicon-based CCD sensor.

In another embodiment of the present invention, the rejuvenation illumination system 102 may include one or more illumination sources 110 configured to generate light suitable for at least partially rejuvenating an imaging sensor 104 degraded by exposure to high energy light, such as EUV or DUV light. In one embodiment, the rejuvenation illumination system 102 may include one or more illumination sources 110 configured to generate illumination having a wavelength suitable for absorption by a substrate of the imaging sensor 104. For example, in the case of a CCD detector having a silicon substrate, the light generated and emitted by the illumination source 110 of the illumination system 102 may include light efficiently absorbed by the silicon substrate such that illumination from the illumination source 110 can adequately heat the sensor 104. For example, light having a wavelength of greater than 900 nm is generally not efficiently absorbed by a silicon substrate of a CCD detector. It is noted, however, that the particular absorption threshold for a particular implementation of the present invention is dictate to the specific absorption characteristics of the sensor 104.

In another embodiment, the rejuvenation illumination system 102 may include one or more illumination sources 110 configured to generate illumination having an energy low enough (i.e., a wavelength large enough) to substantially avoid degradation of the imaging sensor 104. For example, in the case of a CCD detector having a silicon substrate, the light generated and emitted by the illumination source 110 of the illumination system 102 may include light having a wavelength above approximately 350 nm, which is sufficient to avoid causing additional damage to the imaging sensor 104. For instance, the illumination source 110 of the rejuvenation illumination system 102 may include, but is not limited to, any one of near IR light source, a visible light source or a near UV light source.

It is noted herein that in order to provide efficient light absorption by the imaging sensor 104, while avoiding additional degradation of the imaging sensor 104, the one or more illumination sources 110 of the rejuvenating illumination system 102 should be configured to emit light between an absorption threshold and a damage threshold, which are defined by the material properties of the imaging sensor 104. For example, in the case of a CCD sensor having a silicon substrate, the one or more illumination sources 110 of the rejuvenating illumination system 102 may be configured to emit illumination at a wavelength between 350 and 900 nm, which define the damage and absorption thresholds, respectively, for a silicon based CCD detector.

In another embodiment of the present invention, the rejuvenation illumination system 102 includes one or more illumination sources 110 configured to emit illumination having a power level (e.g., 1 watt) capable of heating a substrate above a rejuvenation temperature threshold. In this regard, the rejuvenation temperature threshold is interpreted to as a temperature required to attain a selected level of degradation reversal (i.e., rejuvenation) in a given degraded imaging sensor 104. For example, in the case of a CCD imaging sensor with a silicon substrate, the minimum temperature threshold may be approximately 60° C. In another embodiment, the rejuvenation illumination system 102 includes one or more illumination sources 110 configured to emit illumination capable of limiting the heating of the substrate of a given imaging sensor 104 such that the temperature of the substrate does not exceed a selected degradation threshold. For example, in the case of a CCD imaging sensor with a silicon substrate, the minimum temperature threshold may be approximately 80° C. In a further embodiment, the one or more illumination sources 110 of the rejuvenation illumination system 102 may be configured to heat a substrate of the imaging sensor 104 to a temperature between the absorption and degradation thresholds. For example, in the case of a CCD imaging sensor with a silicon substrate, the illumination source 110 may be configured to heat the silicon substrate to a temperature between 60° and 80° C.

In another embodiment, the rejuvenation illumination system 102 may include one or more illumination sources 110 configured to illuminate the imaging sensor 104 continuously over a selected time interval. For example, the selected time interval may include, but is not limited to one hour. In another embodiment, it is recognized that the time interval may significantly exceed 1 hour. It is further noted herein that following a given rejuvenation illumination process carried out by the present invention, a time for equilibration should be allowed in order to allow the imaging sensor 104 to return to its normal operating temperature prior to a subsequent image/measurement acquisition. For example, the time required for imaging sensor 104 equilibration following rejuvenation may include, but is not limited to, one minute.

In another embodiment, the one or more illumination sources 110 are configured to illuminate the imaging sensor 104 with a series of exposure intervals. In this regard, each exposure of the imaging sensor may last for a selected exposure interval time. Further, the exposure intervals (i.e., ON state) may be separated in time by a series of "OFF" states, wherein the duration of the "OFF" states is also selectable. It is noted herein that the summed time of exposure may include, but is not limited to, one or more hours.

In an alternative embodiment of the present invention, the one or more illumination sources 110 of the rejuvenation illumination system 102 may include one or more pulsed lasers. In this regard, in the case of a silicon based CCD imaging sensor, a short laser pulse of high intensity may act to heat substantially only the silicon of the imaging sensor in the vicinity of the interface between the silicon and the thin transparent film disposed on the top surface of the silicon. It is noted herein that a pulsed laser with a wavelength between 350 and 550 nm will not generally penetrate more than approximately 1 µm into silicon and will heat the interface, film and top layer of silicon. It is further noted herein that since the degradation is caused by effects at the interface and in the transparent film, the present invention acts to provide heat in the imaging sensor architecture where it is effectively used. It is further noted that it is possible to locally heat an exposure region of an imaging sensor to a high temperature (e.g., approximately 300° C.), without significantly raising the temperature of the underlying silicon or detector package. It is further recognized herein that in the pulsed-source case described herein silicon of a CCD imaging sensor will efficiently spread heat laterally. As such, it may be necessary to move the beam between or during pulses in order to rejuvenate the complete active area of the imaging sensor 104. It is further noted that advantage of this embodiment of the present invention includes the ability to achieve much higher temperatures than in the continuous wave case described throughout the present disclosure. Higher achievable temperatures, in turn, lead to more complete imaging sensor rejuvenation in a smaller amount of time, allowing for more frequent rejuvenation and shorter imaging system down times.

In one embodiment of the present invention, the one or more illumination sources 110 of the rejuvenation illumination system 102 may include a light emitting diode. In another embodiment of the present invention, the one or more illumination sources 110 of the rejuvenation illumination system 102 may include a narrow band source, such as, but not limited to, a laser. In one embodiment of the present invention, the one or more illumination sources 110 of the rejuvenation illumination system 102 may include broadband source, such as, but not limited to a broadband lamp.

FIGS. 1A through 1C depict various high-level block diagram views of the various configurations of the system 100 suitable for selectably illuminating one or more portions of an imaging sensor 104, in accordance with embodiments of the present invention.

In one embodiment, as shown in FIG. 1A, the rejuvenation illumination system 102 may include one or more illumination sources 110 aligned off-axis with respect to the normal illumination pathway 106 of the inspection/imaging system 106. Light traveling from the output of the illumination source(s) 110 of the rejuvenation illumination system 102 does not interfere with the normal imaging process carried out by the imaging sensor 104 on the sample 105 (or mask) disposed on stage 109 In this regard, light traveling along the optical pathway defined by the illumination source 110 and the imaging sensor 104 does not interfere with light traveling along the optical pathway 107 (e.g., collection pathway) of the imaging/inspection system 106. In additional embodiments, the system 100 may include one or more optical elements used to direct, focus, or filter illumination emanating from the one or more illumination sources 110. For example, the system 100 may include one or more lenses 103 configured to focus illumination from the illumination sources 110 onto the imaging sensor 104. It is noted herein that the configuration illustrated in FIG. 1A is not limiting as numerous equivalent embodiments are within the scope of the present invention. It is further noted that with respect to the embodiment depicted in FIG. 1A the illumination source 110 may be positioned at numerous positions relative to the imaging sensor 104 provided such positioning allows light emitted by the one or more illumination sources 110 to impinge on the sensor 104 along a direction that is off-axis from the optical pathway of the illumination system of the imaging/inspection system 106.

In another embodiment, as shown in FIG. 1B, the rejuvenation illumination system 102 may include one or more illumination sources 110 and one or more actuatable (e.g., translational or rotational) mirrors 112 configured to selectably establish a temporary optical pathway 116 between the one or more illumination sources 110 and a portion of the imaging sensor 104. For example, a mirror 112 may be disposed on an actuatable stage 114 (e.g., translatable stage or rotatable stage) configured to selectably move the mirror in a manner that allows for the selectable establishment of an illumination pathway 116 between the one or more illumination sources 110 and the imaging sensor 104 during times the sensor 104 is in a non-imaging state, as shown in FIG. 1B. In one embodiment, the actuatable stage may be a manually actuatable stage 114. In another embodiment, actuatable stage 114 may be communicatively coupled to the controller 108. In a further embodiment, the controller is configured to direct the actuatable stage 114 to move the mirror in order to establish the temporary illumination optical pathway 116 described above.

Regarding FIGS. 1A and 1B, in an additional embodiment, the system 100 may include one or more devices suitable for inhibiting light reflected from the imaging sensor 104 from entering the imaging/inspection system 106. It is noted herein that light reflected from imaging sensor 104 and the associated sensor package may cause damage or heating if the reflected light is able to travel into the imaging system 106. As such, in one embodiment, the imaging sensor 104 may be illuminated by the illumination sources 110 at a nonzero angle of incidence. In a further embodiment, the system 100 may include a non-reflective beam stop configured to block light reflected from one or more portions of the imaging sensor 104.

FIG. 1C illustrates a block diagram view of a rejuvenation system 100 equipped with thermal monitoring capabilities, in accordance with one embodiment of the present invention. In one embodiment, a thermal monitoring device 118 (e.g., thermocouple and the like) may be disposed in or on the imaging sensor 104. In another embodiment, the thermal monitoring device 118 is communicatively couple to the controller 108. In a further embodiment, the thermal monitoring device 118 may measure the temperature of one or more portions of the imaging sensor 104 and transmit the measured temperature to the controller 108. In response to the measured temperature, the controller 108 may establish and maintain a temperature of the imaging sensor 104 by directing the output power of the one or more illumination sources 110. For example, in the case of an LED illumination source, the controller 108 may control the current of the LED illumination source in order to control the output power of the illumination source 110 and thereby establish and maintain a desired temperature in the imaging sensor 104.

In a preferred embodiment of the present invention, the imaging system 106 is used in a normal operating mode with exposure of the imaging sensor 104 (e.g., CCD or TDI) to EUV or DUV light. After a fixed period of time of accumulated exposure (e.g., fixed based on anticipated level of degradation of the given time), a given imaging process is completed and a mirror 112 is moved into place and the one or more illumination sources 110 (e.g., laser, lamp or LED) of the rejuvenation system 100 are engaged. The mirror is positioned into a location allowing for the temporary establishment of a rejuvenation illumination pathway 116, allowing the one or more illumination sources 110 to expose at least a portion of the imaging sensor 104 with uniform illumination (e.g., near UV, visible or near IR light). Due to the exposure to the rejuvenating illumination, the imaging sensor 104 may be heated and the temperature may be monitored using a temperature sensor 118 (e.g., thermocouple) embedded in the substrate of the imaging sensor 104, whereby the temperature results are collected by controller 108. Further, in response to the temperature measurements of the temperature sensor 118, the power output of the one or more illumination sources 110 may be controlled by the controller 108 in order to stabilize the imaging sensor 104 at a selected temperature (e.g., 80° C.). Then, the temperature of the imaging sensor 104 may be maintained at the selected temperature for a selected amount of time (e.g., 15 minutes). In one embodiment, during the rejuvenating phase, a new sample may be loaded onto the sample stage 109. Following the heating cycle of the imaging sensor 104 using the rejuvenation illumination system 102, the illumination sources may be turned off, allowing the imaging sensor 104 to cool. Upon reaching a normal operating temperature (e.g., 35° C.), the mirror 112 is moved in a manner to terminate the temporary rejuvenation optical pathway 116, allowing a normal imaging process to be carried out using the imaging sensor 104 and the optical pathway 107.

FIG. 2 illustrates a process flow 200 for rejuvenating an imaging sensor degraded by extreme ultraviolet or deep ultraviolet light, in accordance with one embodiment of the present invention. In step 202, a portion of an imaging sensor of an imaging system is illuminated during a non-imaging state of the imaging sensor with illumination suitable for at least partially rejuvenating the imaging sensor degraded by exposure to at least one of extreme ultraviolet light or deep ultraviolet light. In step 204, the temperature of the imaging sensor is monitored. In step 206, responsive to the monitored temperature of the imaging sensor, the temperature of the imaging sensor may be established or maintained by adjusting a power output level of illumination impinging on the imaging sensor.

It is further contemplated that each of the embodiments of the method described above may include any other step(s) of any other method(s) described herein. In addition, each of the embodiments of the method described above may be performed by any of the systems described herein.

It should be recognized that the various control steps associated with the configuring of the system 100 described throughout the present disclosure may be carried out by controller 108 include a single computer system or, alternatively, a multiple computer system. Moreover, different subsystems of the system 100 may include a computer system suitable for carrying out at least a portion of the steps described above. Further, the one or more computer systems may be configured to perform any other step(s) of any of the method embodiments described herein.

The controller 108 may include, but is not limited to, a personal computer system, mainframe computer system, workstation, image computer, parallel processor, or any other device known in the art. In general, the term "computer system," "computing system(s)," or "computer control system" may be broadly defined to encompass any device(s) having one or more processors, which execute instructions from a memory medium. Program instructions implementing methods such as those described herein may be transmitted over or stored on carrier medium. The carrier medium may be a transmission medium such as a wire, cable, or wireless transmission link. The carrier medium may also include a storage medium such as a read-only memory, a random access memory, a magnetic or optical disk, or a magnetic tape.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

What is claimed:

1. A system comprising:
   an imaging system including an imaging sensor, the imaging system including an optical pathway between the imaging sensor and a sample stage, wherein the imaging system is configured to image one or more samples disposed on the sample stage with at least one of extreme ultraviolet light or deep ultraviolet light;
   a rejuvenation illumination system including one or more illumination sources configured to selectably illuminate a portion of the imaging sensor of the imaging system with illumination for at least partially reversing degradation of the imaging sensor caused by exposure of the imaging sensor to the at least one of extreme ultraviolet light or deep ultraviolet light from the imaging system, wherein the rejuvenation illumination system includes an optical pathway between the one or more illumination sources of the rejuvenation system and the imaging sensor, the optical pathway of the rejuvenation illumination system is aligned off-axis relative to the optical pathway of the imaging system, wherein the one or more illumination sources of the rejuvenation illumination system are configured to generate illumination of at least one wavelength range different from extreme ultraviolet light and deep ultraviolet light from the imaging system; and a temperature sensor disposed on a portion of the imaging sensor; and a controller communicatively coupled to the rejuvenation illumination system and the temperature sensor disposed one the portion of the imaging sensor, wherein the controller is configured to direct the rejuvenation illumination system to illuminate the imaging sensor for one or more illumination cycles during a non-imaging state of the imaging sensor in response to one or more signals from the temperature sensor.

2. The system of claim 1, wherein the imaging sensor comprises:
a semiconductor imaging sensor.

3. The system of claim 1, wherein the imaging sensor comprises:
at least one of a charged coupled device (CCD) or a time delay integration (TDI) sensor.

4. The system of claim 1, wherein the rejuvenation illumination system includes one or more illumination sources configured to generate illumination having a wavelength suitable for absorption by a substrate of the imaging sensor.

5. The system of claim 1, wherein the rejuvenation illumination system includes one or more illumination sources configured to generate illumination having a wavelength large enough to substantially avoid degradation of the imaging sensor.

6. The system of claim 1, wherein the rejuvenation illumination system includes one or more illumination sources configured to generate illumination having a wavelength in at least one of the near infrared band, the visible band and the near ultraviolet band.

7. The system of claim 1, wherein the rejuvenation illumination system includes one or more illumination sources configured to generate illumination having a wavelength between 350 nm and 900 nm.

8. The system of claim 1, wherein the rejuvenation illumination system includes one or more illumination sources configured to emit illumination capable of heating a substrate above a rejuvenation temperature threshold.

9. The system of claim 8, wherein the rejuvenation temperature threshold is 60° C.

10. The apparatus of claim 8, wherein the rejuvenation illumination system includes one or more illumination sources emitting illumination capable of heating the substrate above the rejuvenation temperature threshold and below a degradation threshold.

11. The system of claim 10, wherein the rejuvenation illumination system includes one or more illumination sources emitting illumination capable of heating a substrate between 60° and 80° C.

12. The system of claim 1, wherein the rejuvenation illumination system includes one or more illumination sources configured to illuminate the imaging sensor continuously over a selected time interval.

13. The system of claim 12, wherein the rejuvenation illumination system includes one or more illumination sources configured to illuminate the imaging sensor over the selected time interval, wherein the one or more illumination sources are configured to illuminate the imaging sensor using two or more exposure intervals having a selected time of exposure.

14. The system of claim 1, wherein the rejuvenation illumination system includes one or more pulsed illumination sources configured to illuminate the imaging sensor with a periodic waveform having selected pulse duration and frequency.

15. The system of claim 1, wherein the rejuvenation illumination system includes one or more illumination sources, the one or more illumination sources including at least one of a light-emitting diode, a broadband lamp and a laser.

16. The system of claim 1, wherein the rejuvenation illumination system comprises:
an actuatable mirror configured to selectably establish a temporary illumination pathway between an output of the one or more illumination sources and the one or more imaging sensors.

17. The system of claim 1, wherein the controller is configured to establish a selected temperature of the imaging sensor via the one or more illumination sources of the rejuvenation system in response to the temperature sensor.

18. The system of claim 1, wherein the controller is configured to maintain a selected temperature of the imaging sensor via the one or more illumination sources of the rejuvenation system in response to the temperature sensor.

* * * * *